United States Patent [19]
Del Soldato et al.

[11] Patent Number: 6,040,341
[45] Date of Patent: Mar. 21, 2000

[54] COMPOUNDS AND THEIR COMPOSITIONS HAVING ANTI-INFLAMMATORY AND ANTI-THROMBOTIC ACTIVITIES

[75] Inventors: Piero Del Soldato; Francesco Sannicolo', both of Milan, Italy

[73] Assignee: Nicox S.A., Paris, France

[21] Appl. No.: 09/066,344

[22] PCT Filed: Oct. 29, 1996

[86] PCT No.: PCT/EP36/04696

§ 371 Date: Apr. 29, 1998

§ 102(e) Date: Apr. 29, 1998

[87] PCT Pub. No.: WO97/16405

PCT Pub. Date: May 9, 1997

[30] Foreign Application Priority Data

Oct. 31, 1995 [IT] Italy .................................. MI95A2263

[51] Int. Cl.$^7$ ................................................... A61K 31/21
[52] U.S. Cl. ........................................... 514/509; 558/482
[58] Field of Search ............................... 558/482; 514/509

[56] References Cited

U.S. PATENT DOCUMENTS 5,621,000  4/1997  Arena et al. .
5,700,947  12/1997  Soldato .

FOREIGN PATENT DOCUMENTS 9201668  2/1992  WIPO .
9530641  11/1995  WIPO .
9716405  5/1997  WIPO .

*Primary Examiner*—Samuel Barts
*Attorney, Agent, or Firm*—Nikaido Marmelstein Murray & Oram LLP

[57] ABSTRACT

Compounds and their compositions, of general formula: $A—X_1—NO_2$ are used as medicaments wherein: $A=R(COX)_t$, $t=0$ or $1$; $X=O$ and the remaining substituents are defined in the specification.

7 Claims, No Drawings

COMPOUNDS AND THEIR COMPOSITIONS HAVING ANTI-INFLAMMATORY AND ANTI-THROMBOTIC ACTIVITIES

This application is a 371 of PCT/EP96/04696 filed Oct. 29, 1996.

The present invention relates to new products having anti-inflammatory, analgesic and anti-thrombotic activities.

In particular it relates to inhibitors of cyclo-oxygenase (COX) of the class of Aspirin, i.e. of acetylsalicidic acid or its derivatives in general.

It is known that the anti-inflammatory and anti-thrombotic efficacy of NSAIDs (Non Steroid Anti-Inflammatory Drugs), also known as FANS, but above all their tolerance, seem to be markedly affected by their inhibitor activity of the cyclo-oxygenase (COX) in the inflammatory site as well as in healthy tissue. See for example FASEB Journal 1, 89, 1987; Bioch. Biophys. Acta 1083, 1, 1991. It is generally believed that the stronger a COX inhibitor is the more effective it is.

The disadvantage of these products is that they are toxic.

Furthermore, it is also known that the COX-inhibiting properties seem to depend on some factors bound to the physico-chemical and structural characteristics of the molecules themselves, such as for example the acidic function. See for example J. Pharmacol. Exp. Therap. 196, 226, 1976; Arch. Toxicol. 60, 261, 1987.

The known cyclo-oxygenase inhibitors are generally acids which can be brought back to general structures, including:
- carboxyl acids, either acetylated such as, for example, aspirin and triflusal, or nonacetylated such as, for example, salycilate, diflunisal, salsalate;
- acetic acids, for example diclofenac, indomethacin, tolmetin, sulindac, etodolac, ketorolac;
- propionic acids, such as, for instance, ibuprofen, naproxen, pirprofen, tiaprofenic acid, loxoprofen, indoprofen, oxaprozin, ketoprofen, fenoprofen, fenbufen, flurbiprofen, carprofen, suprofen.

See for example a previous patent application in the name of the applicant PCT/EP 95/01233, herein incorporated by reference, which describes the prior art of the above products.

As said, the disadvantage of these products is that they are very effective but highly toxic.

The importance of the acidic function resides in the fact that the masking of this function in COX inhibitors results in a virtually complete loss of its prostanoid-inhibiting properties. See Drugs 35, 504, 1988.

Products are also known which are highly effective in inhibiting cyclooxygenase and have a low toxicity even though they do not contain the acidic function in their molecule.

These products are known as nitric esters with nonacidic ending. See for example patents WO 94/04484, which describes a particular group of compounds including the well known commercial product diclofenac; WO 94/12463, which describes another specific group of compounds including the commercial products flurbiprofen and indoprofen, PCT/EP 94/03182, which describes another specific group of compounds including the commercial products naproxen and ketorolac.

In a previous patent application in the name of the applicant PCT/EP 95/01233 other nitric esters having a nonacidic termination have been described with various linking groups $X_1$ as specified below. The new linking groups therein described showed advantages from the pharmcological and pharmaceutical viewpoint, in particular pharmaco-cinetic and pharmaco-dynamic viewpoint, since they showed a lower variability of the response. The products described in said patent application were also able to exert an inhibition effect of the inflammation produced by lyposaccaride (LPS) and therefore useful in the septic shock. This result was unexpected since it is well known that the anti-inflammatory products in general do not significantly modify the activity of the nitrosynthetase induced by lypopolysaccarides in the rat and therefore they are not useful in the septic shock.

The technical problem to be solved by the present invention relates to inhibitor products of the COX much more effective in inhibiting the piastrine aggregation induced by arachidonic acid and trombin, the latter having a well known primary patogenetic role even superior to arachidonic acid and other aggregant stimulus, said products having contemporaneously a high gastric tolerability, without provoking adhesions of the gastric intestinal mucose on the treated animals.

The applicant has unexpectedly and surprisingly found a specific class of anti-inflammatory products, as described hereinbelow, having an improved inhibtor activity of the COX combined with a low toxicity.

An object of the present invention are compounds, or their compositions, of general formula:

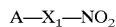

or their salts, for use as medicaments, in particular as anti-inflammatory and antithrombotic agents, having improved efficiency in inhibiting the piastrinic aggregation induced by arachidonic acid and/or trombin, wherein:

$A = R(COX)_t$, wherein t is zero or 1;

$X = O, NH, NR_{1C}$ wherein $R_{1C}$ is a linear or branched alkyl having 1 to 10 C atoms, preferably 1–4 C atoms, or

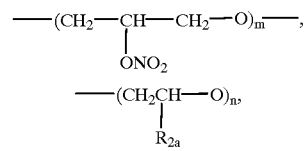

wherein m and n are integers from 1 to 6, preferably m from 1 to 3, and n from 2 to 4; $R_{2a}$ being H, $CH_3$; the linking with $X_1$ can be in any position of the ring, preferably in position 2; —$OCOR_3$ preferably in position ortho with respect to —$COX_0$—;

$X_0 = X$;

R is chosen from:

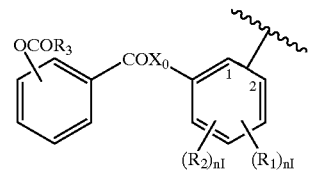

wherein:
$R_1$ is an $OCOR_3$ group, wherein $R_3$ is methyl, ethyl or a linear or branched $C_3$–$C_5$ alkyl, or the residue of a heterocycle with a single ring having 5 or 6 atoms which may be aromatic, partially or totally hydrogenated, containing one or more heteroatoms independently chosen from O, N, and S;

$R_2$ is hydrogen, hydroxy, halogen, a linear or when permissible branched alkyl having 1 to 4 C atoms, a linear or when permissible branched alkoxyl having 1 to 4 C atoms, a linear or when permissible branched perfluoroalkyl having 1 to 4 C atoms, for example trifluoromethyl; nitro, amino, mono- or di-alkylamine in which the alkylamine has 1 to 4 C atoms;

$R_1$ and $R_2$ together are a dioxymethylene group, with the proviso that when X=NH, then $X_1$ is ethylene and $R_2$=H; $R_1$ cannot be $OCOR_3$ in position 2 when $R_3$ is methyl; nI being 0 or 1;

$X_1$ in the formula $A—X_1—NO_2$ is a bivalent connecting bridge chosen from the following:

—YO— where Y is selected from:
- a linear or when permissible branched $C_1$–$C_{20}$ alkylene, preferably having from 1 to 3 carbon atoms;
- a cycloalkylene having from 5 to 7 carbon atoms optionally substituted;

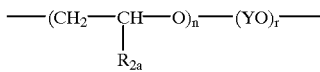

wherein n is an integer from 1 to 6, preferably from 2 to 4; $R_{2a}$ as defined above; r=0 or 1; Y as defined above, preferably $C_1$–$C_{10}$, preferably $C_2$–$C_6$.

The preferred products according to the present invention are those in which t=0, $X_0$ is oxygen; the group having $NO_2$ is in position 2 with respect to $—COX_0$; nI=0; $R_3=CH_3$. In particular the preferred products according to the present invention are the following:

$R_1$ is an $OCOR_3$ group, wherein $R_3$ is methyl, etnyl or a linear or branched $C_3$–$C_5$ alkyl, or the residue of a heterocycle with a single ring having 5 or 6 atoms which may be aromatic, partially or totally hydrogenated, containing one or more heteroatoms independently chosen from O, N, and S;

$R_2$ is hydrogen, hydroxy, halogen, a linear or when permissible branched alkyl having 1 to 4 C atoms, a linear or when permissible branched alkoxyl having 1 to 4 C atoms, a linear or when permissible branched perfluoroalkyl having 1 to 4 C. atoms, for example trifluoromethyl; nitro, amino, mono- or di-alkylamine in which the alkylamine has 1 to 4 C atoms;

$R_1$ and $R_2$ together are a dioxymethylene group, with the proviso that when X=NH, then Y is ethylene and $R_2$=H; $R_1$ cannot be $OCOR_3$ in position 2 when $R_3$ is methyl; nI being 0 or 1

$X_1$ in the formula $A—X_1—NO_2$ is a bivalent connecting bridge chosen from the following:

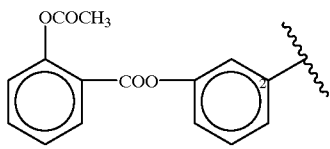

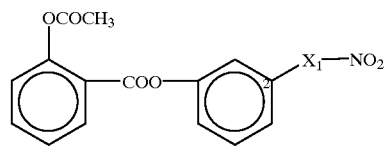

where Y is selected from:
- a linear or when permissible branched $C_1$–$C_{20}$ alkylene, preferably having from 1 to 3 carbon atoms;
- a cycloalkylene having from 5 to 7 carbon atoms optionally substituted; ned in X). All well known synthetic routes for forming these bonds may be used to form this connection.

In the case of the esters, the most direct synthetic route involves a reaction of acyl chlorides R—CO—Cl with halogen alcohols for example HO—Y—Cl, HO—Y—Br, HO—Y—I, in the experimental conditions well known in the art.

The reaction products are converted into the final products by reacting with $AgNO_3$ in acetonitrile, in accordance to what known from the literature.

The general route is as follows:

$R—CO—Cl+HO—Y—Br \rightarrow R—CO—O—Y—Br+AgNO_3 \rightarrow A—X_1—NO_2$ wherein $X_1$=YO.

In the case of amides the synthetic route involves a reaction of said acyl chlorides RCOCl with amino alcohols of the general formula $NH_2—Y—OH$, $NHR_{1C}—Y—OH$ to give amides of the general formula:

$R—CO—NH—Y—OH$ and $R—CO—NHR_{1C}—Y—OH$ in accordance with known methods.

The reaction of said amides with halogenating agents such as, for example, $PCl_5$, $PBr_3$, $SOCl_2$, etc., brings to halogen derivatives of the general formula:

$R—CO—NH—Y—Br(Cl)$ and $R—CO—NR_{1C}—Y—Br(Cl)$.

The latter products by reacting with $AgNO_3$ in acetonitrile in accordance with known literature methods, bring to the final products $A—X_1—NO_2$.

The route may be outlined as follows:

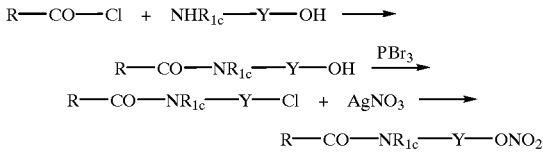

wherein YO is $X_1$.

An alternative route to form the esters is a reaction of the sodium or potassium salts of the acids with the nitric esters of halogen alcohols of the general formula:

$NO_2—O—Y—Cl$ (Br, I)

to directly give the products of the invention.

The reaction route is as follows:

$R—CO—ONa+Br—Y—ONO_2 \rightarrow R—CO—O—Y—ONO_2$ wherein YO is $X_1$.

The following examples are being given only as illustrative explanation but not as a limitation of the present invention.

EXAMPLES

Example 1
Comparison—Preparation of the Products

It was used acetylsalicilic acid ASA available on the market, Aspirin of Bayer.

Example 2
Comparison—Preparation of the Compound $A—X_1—NO_2$, wherein R has the formula below of Aspirin, $X_1$ is $—(CH_2)_4O—$, herein called ANBE, and having general formula:

2-acetoxy-benzoate of (4-nitroxy)butyl

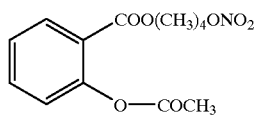

Preparation of the intermediate having formula:

2-acetoxy-benzoate of (4-bromine)butyl

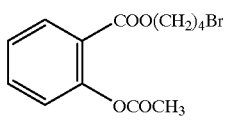

At a solution of:

| acetylsalicilic acid | 15.0 g and |
| dimethylformamide | 50 ml | kept at 0° C. under nitrogen stream it is added portionwise: 2.6 g of NaI (80% by weight suspension in vaseline oil). The mixture was left under stirring for 1 hour and then was dropped in 5 hours, at 25° C. in a stirred solution of:

| 2,2'-dibromo-butane | 27.0 g and |
| dimethylformamide | 50 ml |

The mixture was left under stirring for 3 days, then was dried at reduced pressure. The residue was treated with:

| water | 50 ml |
| dichloromethane | 50 ml |

The phases were separated and the aqueous phase was further extracted in 10 ml of dichloromethane.

The pooled organic phases were washed with water (3×25 ml), dried (MgSO$_4$), decoloured with animal charcoal (1 g), and brought to dryness in vacuum.

The residue (26.0 g) was used crude for the next reaction. Preparation of ANBE

At a solution of

| ASA—(CH$_2$)$_4$Br | 26.0 g |
| acetonitrile | 65 ml | kept at room temperature and sheltered from light, was added

| silver nitrate | 21.0 g |

After 2 days under stirring were added 4.3 g of silver nitrate.

After 2 further days under the same conditions the insoluble salts were filtered and the filtrate was freed of the solvent at reduced pressure.

A residue of 18.0 g was obtained and the chromatography on a silica gel column (500 g of silica) eluting with a toluol/ethyl acetate 95/5 v/v mixture was carried out.

The fractions resulted uniform for TLC (Thin Layer Chromatography) analysis and were pooled and brought to dryness and gave 15.0 g of ANBE.

The $^1$H NMR (CDCl$_3$) (80 MHz) analysis showed the following data: 2.28 (3H, s); 1.2 (4H, m); 4.30 (2H, t); 4.50 (2H, t); 7.3 (3H, m); 7.95 (1H, dd). The IR analysis (Nujol) provided the following results: $\upsilon_{OCO}=1780$ cm$^{-1}$; $\upsilon_{COO}=1725$ cm$^{-1}$; $\upsilon_{ONO2}=1641$ e 1287 cm$_{-1}$. Mass spectrometry gave a molecular weight value of 297.

Example 3

Preparation of the compound $A—X_1—NO_2$ wherein R has the formula below, $X_1$ is $—(CH_2)O$, herein called ANMPE having formula:

2-acetoxy-benzoate of (3-nitroxymetyhyl)fenyl

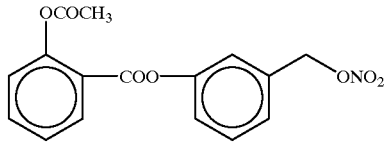

Preparation of the intermediate of formula

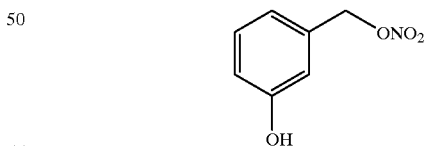

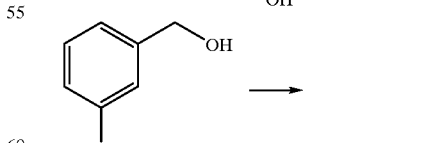

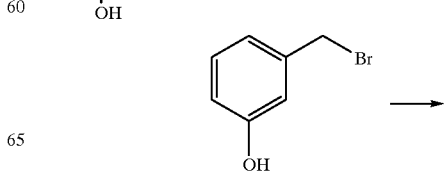

-continued

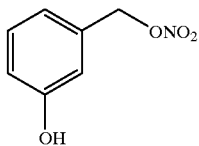

In a 1 l flask were added:

| | |
|---|---|
| 3-OH-benzyl alcohol | 28.1 g (0.226 mols) |
| Methylene chloride | 85 ml |
| HBr (48% by weight in water) | 140 ml | and were kept under stirring at room temperature for 1 hour and half.

At the end the phases were separated and the aqueous phase was further extracted with methylene chloride (about 50 ml).

The pooled organic phases were washed twice with:

| | |
|---|---|
| Distilled water | 100 ml |
| Solution of NaHCO$_3$ at 5% (w/v) | 50 ml |

Then it was anhydrified on MgSO$_4$ and was brought to dryness obtaining a residue equal to 34.13 g of crystalline solid.

The product was characterized by TLC analysis, by using a toluol/ethylacetate 7/3 v/v mixture as eluent.

The so obtained product is used immediately for the following reaction.

In a 1 l flack provided with stirrer, termometer, dropping system were added:

| | |
|---|---|
| Previous reaction residue | 34 g |
| Acetonitrile | 100 ml |

In the dropping system it was charged a solution of:

| | |
|---|---|
| Silver nitrate | 38.5 g |
| Acetonitrile | 60 ml | and it was dropped in about 2 hours, keeping the flask sheltered from light and cooling on a water bath.

The temperature was maintained between 20 and 30° C.

It was left to react for about 15 hours.

Then it was filtered and the filtrate was dried; at the residue was added etylacetate, about 500 ml, then silica (50 g) and coal (3 g).

The filtrate was dried again and a charomatography on about 300 g of silica using toluol as eluent was carried out by using the chromatographic system indicated above.

11.7 g of product were obtained (dark oil) and characterized by TLC.

Preparation of ANMPE

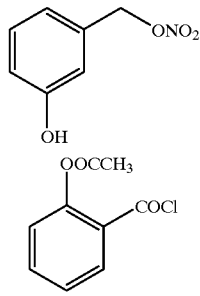

In a 250 ml flask provided with stirrer, termometer, dropping system were introduced:

| | |
|---|---|
| 3-hydroxybenzylnitrate | 4.95 g |
| potassium carbonate | 7.0 g |
| etylacetate | 50 ml |

It was cooled at 0° C. and dropped under nitrogen stream in 15 minutes a solution of:

| | |
|---|---|
| acetylsaliciloil chloride | 5.01 g |
| ethylacetate | 20 ml |

At the end of the dropping it was left to react for about 4 hours at 20° C.

The reaction was made in TLC (toluol ethylacetate 9/1 v/v).
At the end 70 ml of distilled water was added.
The phases were separated, the aqeuous phase was extracted again with 30 ml of ethylacetate and the pooled organic phases were washed with water (30 ml) containing sodium chloride (10 g).
The organic phases were then anhydrified on magnesium sulphate and dried; a 8.9 g residue was obtained (yellow oil) which solidifies for cooling at 0° C. By crystallization from isopropilic ether 6.5 g of ANMPE were obtained at the pure state. The $^1$H NMR (CDCl$_3$) (80 MHz) analysis gave the following data: 2.34 (3H, s); 5.45 (2H, s); 7.05–7.75 (7H, m); 8.24 (1H, dd).

Example 4

Pharmacological Examples

The products prepared above were characterized by a pharmacological viewpoint.
In the in vivo studies (for example toxicity) the products obtained above were administered in form of suspension in carboxymethylcellulose 1–2% by weight.
For the in vitro tests (piastrinic tests) the nitroderivatives, 1 mmol, were dissolved in dimethylsulfoxide and then diluted according to the concentrations listed in the Table.
Aspirin ASA 30 mmols was dissolved in a mixture of etanol:H$_2$O in the range 1:10 by volume and then diluted according to the concentrations listed in the Table.
The samples, obtained without adding the substance under examination (ASA, ANBE, ANMPE), did not show any significant reply.

Toxicity

The acute toxicity was evaluated through oral subministration of a single dose of 1, 3, 10, 30, 100, 200 mg/Kg of product in groups of 10 little rats.

The lethality incidence and the appearance of toxic sinthomatology were noted within a period of 14 days. Also after administration of a dose of 200 mg/Kg the animals did not show any apparent toxicity both with ANMPA and with ANBE.

Tolerability

The gastric tolerability was evaluated through oral subministration in the rat measuring the seriousness of the gastropathie induced according to the criterium indicated by Wallace et al. (Am. J. Physiol. 259, G642, 1990).

Piastrinic Tests

Anti-Aggregating Piastrinic Activity (Anti-thrombotic Activity)

The anti-aggregating piastrinic activity was evaluated in vitro on human piastrines stimulated by trombin or by arachidonic acid according to the method described by Bertele et al. (Science 220, 517, 1983).

COX Inhibition (Anti-inflammatory Activity)

The inhibition activity of the cyclooxygenases was determined in human piastrines according to the method described by Patrono et al (Thrombosis Res. 17, 317, 1980). The enzimatic activity was expressed as level of Tromboxan B2 ($T_xB2$) and measured in ng/ml.

Piastrinic Adhesion

The inhibition activity of the piastrinic adhesion was evaluated according to the method described by Bellavite et al. (Anal. Biochem. 216, 444, 1994).

Intracellular Piastrinic Calcium

The effect of the compounds of the invention or comparison compounds on the calcium concentration inside the piastrine was measured according to the method of Pollock et al. (Biochem. J. 235, 869, 1986).

Indeed the gastric tolerance tests have shown that already at doses of 50–100 mg/Kg ASA induced severe damages in the intestinal gastric mucose of the treated animals. On the contrary ANMPE and ANBE, also when administered at doses of 250–500 mg/Kg did not produce relevant damages.

As regards the other piastrinic tests:

piastrinic adhesion and intracellular piastrinic calcium, only ANMPE resulted efficient in inhibiting significantly and in a dose-dependent way (from $10^{-5}$ to $10^{-4}$ M) both pathological processes.

On the contrary it was not possible to see any inhibiting effect with other compounds under examination.

We claim:

1. A compound of the formula:

$$A—X_1—NO_2$$

or salts, wherein;

A=R(COX)$_t$, wherein t=0 or 1;

X=O, NH, NR$_{1c}$, wherein R$_{1c}$ is a linear or branched C$_1$–C$_{10}$ alkyl group $$—(CH_2CH—CH_2—O)\overline{m}—,\ \text{or}\ (CH_2CH—O)\overline{n}—,$$
$$\qquad\qquad |\qquad\qquad\qquad\qquad\qquad |$$
$$\qquad\qquad ONO_2\qquad\qquad\qquad\quad R_{2a}$$

wherein m and n are an integer from 1 to 6; wherein R$_{2a}$ is H or CH$_3$; and wherein the linking with X$_1$ can be in any position of the ring;

TABLE 1

| | | PIASTRINIC AGGREGATION (%)[1] | | |
|---|---|---|---|---|
| COMPOUND | CONCENTRATION(M) | INDUCED BY ARACHIDONIC ACID | INDUCED BY TROMBIN | COX INHIBITION (%)[1] |
| ASA (Ex. 1) | $10^{-5}$ | 40 | 100 | — |
| ASA (Ex. 1) | $5.10^{-5}$ | — | — | 3 |
| ASA (Ex. 1) | $10^{-4}$ | 0 | 100 | 1 |
| ASA (Ex. 1) | $10^{-3}$ | — | 80 | — |
| ANBE (Ex. 2) | $10^{-5}$ | 100 | — | 80 |
| ANBE (Ex. 2) | $5.10^{-5}$ | — | — | 70 |
| ANBE (Ex. 2) | $10^{-4}$ | 50 | 60 | 30 |
| ANBE (Ex. 2) | $10^{-3}$ | 20 | 50 | — |
| ANMPE (Ex. 3) | $10^{-5}$ | 60 | 70 | 5 |
| ANMPE (Ex. 3) | $5.10^{-5}$ | 10 | 40 | 2 |
| ANMPE (Ex. 3) | $10^{-4}$ | 0 | 0 | — |

[1]% REFERRED TO CONTROLS (FOR ADDING OF THE AGGREGATING SUBSTANCE ONLY)

RESULTS

From the results of the Table, it can be seen that ANMPE (compound of the invention) is much more efficient with respect to ASA and ANBE in the inhibition of the piastrinic aggregation induced by arachidonic acid. In the case of ANMPE it is higher than ANBE and similar to ASA.

Nevertheless in the piastrinic aggregation induced by trombin, which higher patogenetic value is known with respect to the arachidonic acid or other aggregating stimulus, the ANMPE gives values surprisingly higher both with respect to ANBE and ASA.

For the COX inhibition properties, the product of the invention ANMPE shows activities similar to ASA, but well higher with respect to ANBE.

This is much more surprising if we consider that ANMPE as well as ANBE, but differently from ASA, it is very well tolerated in the gastric mucosa.

R is:

[chemical structure showing two aromatic rings with substituents OCOR$_3$, COX$_0$, (R$_2$)$_{nI}$, (R$_1$)$_{nI}$]

wherein:
X$_0$=X;
R$_1$ is OCOR$_3$; wherein R$_3$ is methyl, ethyl, linear or branched C$_3$–C$_5$ alkyl, or the residue of an etherocycle with only one ring having 5 or 6 atoms which can be aromatic, partially or completely hydrogenated, containing one or more ethero-atoms selected independently among O, N and S;

$R_2$ is hydrogen, hydroxy, halogen, linear or branched $C_{1-4}$ alkyl, linear or branched $C_1$–$C_4$ alkoxyl; a linear or branched $C_1$–$C_4$, perflouroalkyl, nitro, amino, mono- or dialkylamine with $C_{1-4}$ alkyl; or $R_1$ and $R_2$ together are dioxymethylene group;

$n_f$ is an integer 0 or 1;

$X_1$ in the formula A—$X_1$—$NO_2$, is a bivalent connecting bridge selected from the group consisting of —YO— where Y is a linear or branched $C_{1-20}$ alkylene, or a substituted or unsubstituted $C_{5-7}$ cycloalkylene; and

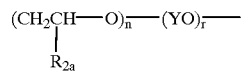

wherein n is an integer from 1 to 6, $R_{2a}$ is an defined above; Y is as defined above, and r=0 or 1;

with the proviso that when X=NH, then Y is only ethylene and $R_2$ is hydrogen; and with the proviso that $R_1$ cannot be $OCOR_3$, in position 2 when $R_3$ is methyl.

2. The compound according to claim 1, wherein R is

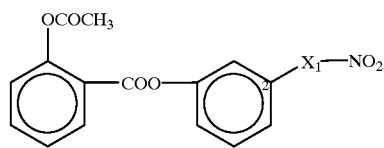

wherein —$X_1$—$NO_2$ is —$CH_2$—$ONO_2$, —$CH_2CH_2CH_2CH_2ONO_2$, —$CH_2CH_2ONO_2$, —$CH_2CH_2OCH_2CH_2ONO_2$, or —$CH_2CH_2OCH_2ONO_2$.

3. The compound according to claim 1, wherein X=$NR_{1c}$ wherein $R_{1c}$ is a linear or branched $C_1$–$C_4$ alkyl group.

4. A composition comprising the compound according to claim 1 or claim 2 and a pharmaceutically acceptable excipient.

5. A method for the treatment of inflammation comprising administering the composition of claim 4.

6. A method for the treatment of thrombosis comprising administering the composition of claim 4.

7. A method for the treatment of septic shock comprising administering the composition of claim 4.

* * * * *